United States Patent [19]

Dickakian

[11] Patent Number: 5,110,997
[45] Date of Patent: May 5, 1992

[54] PROCESS FOR PREVENTING FOULING IN THE PRODUCTION OF ETHYLENE DICHLORIDE

[75] Inventor: Ghazi B. Dickakian, Kingwood, Tex.

[73] Assignee: Exxon Chemical Patents Inc., Linden, N.J.

[21] Appl. No.: 688,053

[22] Filed: Apr. 19, 1991

[51] Int. Cl.$^5$ .................. C07C 17/38; C07C 17/15
[52] U.S. Cl. ........................... 570/222; 570/262; 570/103; 203/6; 203/7; 203/8; 203/9
[58] Field of Search ............... 570/222, 262, 103; 203/6, 7, 8, 9

[56] References Cited

U.S. PATENT DOCUMENTS

Re. 26,330  1/1968  Colfer ..................... 203/6
4,422,953 12/1983  Grace et al. ............. 203/7

Primary Examiner—Howard T. Mars
Attorney, Agent, or Firm—R. L. Graham

[57] ABSTRACT

A method of inhibiting fouling in a crude ethylene dichloride stream comprises introducing into the stream an inhibiting amount of an antifoulant selected from (A) an acylated amine (e.g., reaction product of polyisobutylene and maleic anhydride) and a polyamine (B) magnesium alkyl aryl sulfonate, and (C) a mixture of A and B.

15 Claims, No Drawings

PROCESS FOR PREVENTING FOULING IN THE PRODUCTION OF ETHYLENE DICHLORIDE

FIELD OF THE INVENTION

This invention relates generally to a process for preventing the fouling of equipment used in manufacture of ethylene dichloride (EDC), which in turn is used to produce vinyl chloride monomer (VCM). Specifically, the invention relates to the prevention of fouling of a direct chlorination or an oxychlorination unit of an ethylene dichloride production system.

DESCRIPTION OF PRIOR ART

In the production of vinyl chloride monomer (VCM), ethylene, oxygen and HCl are reacted in a direct chlorination or an oxychlorination unit to produce ethylene dichloride (EDC), which is then processed in a cracking unit to form the VCM. The plant normally includes recycling facilities to recover additional EDC from the bottoms of the various units thereby increasing total EDC recovery.

Serious fouling occurs in the various units handling the liquid EDC. For example, in the primary EDC Recovery Unit, fouling occurs in the distillation trays and the transfer facilities, particularly the retort furnace. EDC fouling is particularly serious in the liquid phase of EDC in the primary EDC Recovery Unit, the EDC Recovery Tar Still, and the EDC Recycle Tar Still. It is not uncommon for the fouling to require plant shutdown after only a few days of operation.

The fouling is believed to be due to highly chlorinated and/or oxygenated polymeric materials which are incompatible in the EDC stream.

In accordance with the present invention, an oil-soluble (preferably overbased) magnesium alkyl aromatic sulfonate and/or reaction product of a dicarboxylic acid and maleic anhydride (PIBSA-PAM) are used as an antifoulant for EDC production facility.

Organic sulfonic acids or alkyl arylsulfonate salts have been used in various operations. U.S. Pat. No. 3,328,283 discloses the use of organic sulfonic acid or alkyl arylsulfonate salts in combination with a partial ester. U.S. Pat. No. 3,328,284 discloses the use of an alkyl aro-sulfonate with an oxyalkylated phenolic compound. The alkyl arylsulfonates disclosed in these patents are used as antifoulants for petroleum refining and not to mitigate fouling of the type encountered in EDC production.

Overbased alkyl arylsulfonates have been used as antifoulants for heat transfer oils. Heat transfer oils, however, are refined oils that do not contain the polymeric antifoulants of the type encountered EDC production and therefore, such applications of the overbased sulfonates are not particularly relevant to the present invention. The transfer oil patents of the prior art include U.S. Pat. Nos. 3,554,914, 3,920,572, and 3,958,624.

Antifoulant processes to reduce carbonaceous deposits include those disclosed in U.S. Pat. No. Re. 26,330 wherein deposit formation in refinery units is inhibited by incorporating in the feed stock a small percentage of an acylated amine prepared by reacting a hydrocarbon substituted succinic acid with an alkylene amine. U.S. Pat. No. 4,195,976 discloses a system wherein fouling of process equipment by an oil stream in refinery operations is reduced by incorporating in the feed from 0.001 to 2 wt % of a bis-oxazoline reaction product of polyisobutenylsuccinic anhydride with a 2,2 disubstituted-2-amino-alkanol, such as tris-hydroxy methylaminomethane. Neither of these references relate to inhibiting fouling of the type (e.g., aliphatic polymers with oxygen and chlorine) encountered in EDC and/or VCM production operations. Fouling in refinery operations is generally caused by asphaltene fouling which consists of polycondensed aromatics.

SUMMARY OF THE INVENTION

It has been discovered that by adding an effective amount of an improved antifoulant to an EDC recovery or distillation unit, fouling by chlorinated/oxygenated polymeric materials is substantially reduced. The antifoulant is soluble in the liquid bottoms of the EDC Recovery Unit and protects the facilities in which the bottom liquids contact, including reboilers, heat exchangers, transfer pipes, heating coils, and the like. These facilities are normally operated at temperatures ranging from 100 to 400 degrees F., preferably 200 to 350 degrees F.

The antifoulant usable in the method of the present invention comprises any one of the following:

(A) an oil-soluble acylated amine which is the reaction mixture of (i) an olefin polymer of C2 to C10 monoolefin having a molecular weight of 300 to 5000 reacted with a C4 to C10 mono-unsaturated dicarboxylic acid material, and (ii) a basic reactant selected from the group consisting of an amine, amino alcohol, and mixtures thereof; or (B) an oil-soluble (preferably overbased) magnesium alkyl aromatic sulfonate; or (C) a blend of from 10 to 90 weight percent of antifoulant A and from 90 to 10 weight percent of antifoulant B.

The preferred antifoulant for use in the EDC production operations is the antifoulant blend C described above. The antifoulant is introduced into the crude EDC feed stream at a concentration of 10 to 500 PPM, preferably 25 to 300 PPM, based on the weight of the EDC feed. The antifoulant has a boiling point below EDC and thus remains in the unit bottoms to protect reboilers, trays, tubes, pipes, etc.

DESCRIPTION OF THE PREFERRED EMBODIMENTS

As mentioned above, the antifoulant for use in the process of the present invention may be as follows: an acylated amine (referred to herein as Antifoulant A); a magnesium sulfonate (referred to herein as Antifoulant B), or a blend of both (referred to herein as Antifoulant C). These three Antifoulants will be described separately.

Acylated Amine (Antifoulant A)

The acylated amine antifoulant is the reaction product of (a) a C2-C10 mono-olefin polymer having a molecular weight of 300 to 5000, substituted with a C4 to C10 mono unsaturated dicarboxylic acid material; and (b) a basic amine reactant, preferably a polyalklamine.

The long chain hydrocarbon polymer substituted dicarboxylic acid material, i.e., acid or anhydride, or ester, used in the invention includes long chain, generally a polyolefin, substituted preferably with 1.05 to 1.25 per mole of polyolefin of an alpha or beta unsaturated C4 to C10 dicarboxylic acid, or anhydride or ester thereof, such as fumaric acid, itaconic acid, maleic acid, maleic anhydride, chloromaleic acid, dimethyl fumarate, chloromaleic anhydride, etc.

Preferred olefin polymers for reaction with the unsaturated dicarboxylic acids are polymers comprising a major molar amount of C2 to C10, e.g., C2 to C5 monoolefin. Such olefins include ethylene, propylene, butylene, isobutylene, pentene, octene-1, styrene, etc. The polymers can be homopolymers such as polyisobutylene, as well as copolymers of two or more of such olefins such as copolymers of ethylene; etc. Other copolymers include those in which a minor molar amount of the copolymer monomers, e.g., 1 to 10 mole %, is a C4 to C18 non-conjugated diolefin, e.g., a copolymer of isobutylene and butadiene; or a copolymer of ethylene, propylene, and 1,4-hexadiene; etc.

In some cases, the olefin polymer may be completely saturated, for example an ethylene-propylene copolymer made by a Ziegler-Natta synthesis using hydrogen as a moderator to control molecular weight.

The olefin polymers will have a number average molecular weight within the range of about 300 and about 5000, preferably between about 400 and about 2000. Particularly useful olefin polymers have number average molecular weights within the range of about 500 and about 1200 with approximately one terminal double bond per polymer chain. An especially useful starting material is polyisobutylene. The number average molecular weight for such polymers can be determined by several known techniques.

Process for reacting the olefin polymer with the C4 unsaturated dicarboxylic acid, anhydride or ester are known in the art. For example, see U.S. Pat. Nos. 3,361,673; 3,087,436; 3,712,892; 3,272,746; 3,245,707; 3,231,587; 3,912,764; 4,110,349; and 4,234,435.

Useful amine compounds for neutralization of the hydrocarbon polymer substituted dicarboxylic acid material include mono and polyamines of about 2 to 30 e.g., 3 to 20, total carbon atoms and about 1 to 12, e.g., 2 to 8 nitrogen atoms in the molecule. These amines may be hydrocarbyl amines or may be hydrocarbyl amines including other groups, e.g., hydroxy groups, alkoxy group, amide groups, nitriles, imidazoline groups, and the like. Hydroxy amines with 1 to 6 hydroxy groups, preferably 1 to 3 hydroxy groups are particularly useful. Preferred amines are aliphatic saturated amines, including those of the general formulas:

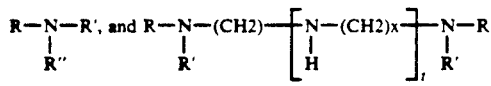

wherein R, R', and R'' are independently selected from the group consisting of hydrogen, C1 to C25 straight or branched chain alkyl radicals, C1 to C12 alkoxy C2 to C6 alkylene radicals, C2 to C12 hydroxy amino alkylene radicals, and C1 to C12 alkylamino C2 to C6 alkylene radicals. Each x can be the same or a different number of from 2 to 6, preferably 2 to 4; and t is a number of from 0 to 10, preferably 2 to 7.

Non-limiting examples of suitable amine compounds include: 1,2-diaminoethane; 1,3-diaminopropane; 1,4-diaminobutane; 1,6-diaminohexane; polyethylene amines such as diethylene triamine; triethylene tetramine; tetraethylene pentamine; polypropylene amines such as 1,2-propylene diamine; di-(1,2-propylene)triamine; di(1,3-propylene) triamine N,N-dimethyl-1, 3-diaminopropane; N,N-di(2-aminoethyl) ethylene diamine; N,N-di-(2-hydroxyethyl)-1, 3-propylene diamine; 3-dodecyloxypropylamine; N-dodecyl-1, 3-propane diamine; tris hydroxymethylaminomethane (THAM); diisopropanol amine; diethanol amine; triethanol amine; mono-, di, and tri-tallow amines; amino morpholines such as N-(3-aminopropyl) morpholine; etc.

Other useful amine compounds include alicyclic diamines such as 1,4-di(aminomethyl) chyclohexane, heterocyclic nitrogen compounds such as imidazolines, and N-aminoalkyl piperazines. Non-limiting examples of such amines include 2-pentadecyl imidazoline; N-(2-aminoethyl) piperazine; etc.

Useful amines also include polyoxyalkylene polyamines such as those of the formulae:

(i) NH2 --- alkylene -(-O-alkylene -)m-NH2 where m has a value of about 3 to 70 and preferably 10 to 35; and (ii) R-(-alkylene-(-O-alkylene-)n-NH2) a where n has a value of about 1 to 40 with the provision that the sum of all the n's is from about 3 to 70 and preferably from about 6 to 35 and R is a substituted saturated hydrocarbon radical of up to ten carbon atoms wherein the number of substituents is represented by "a" which is a number from 3 to 6. The alkylene groups in either formula (i) or (ii) may be straight or branched chains containing about 2 to 7, and preferably about 2 to 4 carbon atoms.

The polyoxyalkylene polyamines preferably polyoxyalkylene diamines and polyoxyalkylene triamines, may have average molecular weights ranging from about 200 to about 4000 and preferably from about 400 to about 2000. The preferred polyoxyalkylene polyamines include the polyoxyethylene and polyoxypropylene diamines and the polyoxpropylene triamines having average molecular weights ranging from about 200 to 2000. The polyoxyalkylene polyamines are commercially available and may be obtained, for example, from the Jefferson Chemical Company, Inc., under the trade name "Jeffamines D-230, D-400, D-1000, D-2000, T-403", etc.

The amine is readily reacted with the dicarboxylic acid material, e.g., alkenyl succinic anhydride, by heating an oil solution containing 5 to 95 wt. % of dicarboxylic acid material to about 100 to 250 degrees C., preferably 125 to 175 degrees C., generally for 1 to 10 e.g., 2 to 6 hours until the desired amount of water is removed. The heating is preferably carried out to favor formation of imides or mixtures of imides and amides, rather than amides and salts. Reaction ratios can vary considerably, depending upon the reactants, amounts of excess amine, type of bonds formed, etc. Generally from 0.2 to 2, preferably about 0.3 to 1.0, e.g., 0.4 to 0.8 mole of amine, e.g., bi-primary amine is used, per mole of the dicarboxylic acid moiety content e.g., grafted maleic anhydride content. For example, one mole of olefin reacted with sufficient maleic anhydride to add 1.10 mole of maleic anhydride groups per mole of olefin when converted to a mixture of amides and imides, about 0.55 moles of amine with two primary groups would preferably be used, i.e., 0.50 mole of amine per mole of dicarboxylic acid moiety.

The preferred amine antifoulants are those derived from polyisobutylene substituted with succinic anhydride groups and reacted polyethylene amines, e.g., tetraethylene pentamine, pentaethylene hexamine, polyoxyethylene and polyoxypropylene amines, e.g., poloxypropylene diamine, trismethylolaminomethane, and combinations thereof. One particularly preferred dispersant combination involves a combination of (a) polyisobutene substituted with succinic anhydride groups and reacted with (b) a hydroxy compound, e.g., pentaerythritol, (c) a polyoxyalkylene polyamine, e.g., polyoxypropylene diamine, and (d) a polyalkylene polyamine, e.g., polyethylene diamine and tetraethylene pentamine using about 0.3 to about 2 moles each of (b) and (d) and about 0.3 to about 2 moles of (c) per mole of (a) as described in U.S. Pat. No. 3,804,763. Another preferred combination involves the combination of (a) polyisobutenyl succinic anhydride with (b) a polyalkylene polyamine, e.g., tetraethylene pentamine, and (c) a polyhydric alcohol or poly-hydroxy-substituted aliphatic primary amine e.g., pentaerythritol or trismethylolaminomethane as described in U.S. Pat. No. 3,362,511.

MAGNESIUM SULFONATE (ANTIFOULANT B)

Magnesium sulfonates are prepared from sulphonic acids or mixtures thereof, or their metal salts. Suitable oil soluble sulfonic acids are preferably aromatic compounds. Especially suitable sulfonic acids are the oil soluble petroleum sulfonic acids commonly referred to as "mahogany acids", aryl sulfonic acids and alkaryl sulfonic acids. Examples of such acids are dilauryl benzene sulfonic acid, lauryl cetyl benzene sulfonic acid, paraffin-substituted benzene sulfonic acids, such as polybutene alkylated benzene sulfonic acids and polypropylene alkylated benzene sulfonic acids. Other suitable examples include diparaffin wax-substituted phenol sulfonic acids, acetyl chlorobenzene sulfonic acids, cetyl-phenol disulphide sulfonic acids, cetyl-phenol mono sulphide sulfonic acids and cetoxy capryl benzene sulfonic acids. Many oil soluble sulfonic acids are described at length in the literature. See for examples, U.S. Pat. Nos. 2,616,604; 2,626,207; and 2,767,209. The neutral sulfonates which may be overbased preferably have the following formula

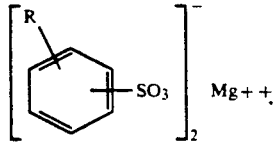

wherein R is an alkyl or haloalkyl having from 12 to 45 carbon atoms, preferably between 16 to 30 carbon atoms, most preferably from 18 to 28 carbon atoms. R preferably is a straight chain aliphatic hydrocarbon radical which may have two homologs present, but may be a branched or mixed alkyl group. The benzene ring of the sulfonic salt may have in addition to R other substituents such as alkyl, hydroxy, halo, nitro groups, or mixtures of these. Typical examples of the sulfonic acids used in preparing the sulfonates include in addition to those mentioned above are alkyl toluene sulfonic acid, alkyl xylene sulfonic acid and the dialkyl benzene sulfonic acid such di-dodecyl benzene sulfonic acid.

The molecular weight of the neutral magnesium alkyl aryl sulfonate may range from 200 to 3000, with 600 to 2000 being preferred for the alkyl benzene sulfonates with 600 to 1200 being the most preferred.

The position of the alkyl group and the sulfonate on the benzene ring in relation to each other is not critical. Secondary alkyl groups may also be present. The alkyl benzene magnesium sulfonate is preferably overbased with an alkaline earth metal, preferably magnesium.

The magnesium overbased alkyl benzene magnesium sulfonates which are preferred for use in the present invention may be prepared by processes described in the literature. An example of one process is as follows:

(a) reacting benzene with an olefin by a simple alkylation process;

(b) sulfonating the alkyl benzene to form neutral alkyl benzene magnesium sulfonic acid;

(c) overbasing the alkyl benzene sulfonic acid with magnesium to produce a product having a total base number (TBN) between 50 an 700 mg KOH/gram, preferably between 300 and 600 mg KOH/gram.

Various methods of overbasing sulfonates to form overbased alkaline earth sulfonates have been reported in the literature.

One such method which is described in UK Patent No. 1,551,820 employs a magnesium alkoxide as an intermediate in magnesium overbasing. This route to magnesium overbasing is not now used extensively.

The most common procedure for the preparation of overbased magnesium sulfonate is from magnesium oxide, as described generally below:

1) Adding to an inert, volatile solvent which may be aliphatic, aromatic or chlorinated,
   a) an oil soluble sulfonic acid or salt thereof,
   b) sufficient magnesium oxide to form the desired product,
   c) an hydroxy containing compound (e.g., methanol),
   d) water,
   e) a non-volatile diluent oil, and
   f) a promoter.

2) Treating the above mixture with carbon dioxide, at a temperature of between 50 degrees F. and the reflux temperature of the mixture, until the absorption of carbon dioxide virtually ceases. Usually 0.5 to 1.1 moles and more usually 0.6 to 0.9 moles of carbon dioxide are absorbed by the mixture of every mole of overbasing magnesium.

3) The volatile components are then removed by distillation to typically 160 degrees C. and finally the mixture is subjected to a vacuum to ensure complete removal of the volatiles.

4) The unreacted solids are then removed by either filtration or centrifugation.

5) Further addition of diluent oil may be added to obtain the desired product.

Many different promoters may be employed to facilitate the reaction towards forming the overbased magnesium sulfonates. The role of some of these promoters is not fully understood, but without them the rate and degree of reaction is substantially reduced. Typical promoters include amines (e.g., ethylene diamine), ammonia or ammonium compounds, carboxylic acids, amine salts of carboxylic acids, and succinic anhydride derivatives. These promoters are described in the patent literature.

The use of sufficient sulfonic acid or its salt, and sufficient magnesium oxide with one of the promoters are used in the above process produces a high alkalinity overbased magnesium sulfonates with Total Base Numbers of 50 to 700, preferably 300 to 600 mg KOH/g.

BLEND OF AMINE ANTIFOULANT AND MAGNESIUM ANTIFOULANT SULFONATE (ANTIFOULANT C)

Antifoulant C is prepared by mixing Antifoulants A and B as follows: 10 to 90 wt. % Antifoulant A and 90 10 wt. % of Antifoulant B, preferably 20 to 80 wt. % of Antifoulant A and 80 to 20 wt. % of Antifoulant B, and most preferably 30 to 70 wt. % of A and 70 to 30 wt. % of B. The mixture is carried in a solvent such as kerosene, wherein the concentration of the actives ranges from 10 to 50 wt. %, and preferably 25 to 35 wt. %.

OPERATIONS

In operation, the antifoulant (A, B, or C) is formulated in a suitable solvent such as kerosene and introduced into the EDC production system to protect equipment exposed to crude EDC at temperatures between 200 to 400 degrees F. The formulation may include other additives such as an antioxidants, antipolymerants, metal deactivators. The concentration of the antifoulant may range from 10 to 500 PPM, preferably 25 to 300 PPM based on the weight of the EDC feed stream.

The locations of the antifoulant introduction will include the crude ethylene dichloride feed to the EDC Recovery Tower which is generally operated at 200 to 400 degrees F. and also include the feed to the EDC Tar Still operated at 200 to 400 degrees C. The term "crude ethylene dichloride" refers to unpurified EDC which leaves the chlorination of oxychlorination units. Crude EDC also refers to the feed stream for the EDC Tar Still. These units may be considered distillation separation units which separate the crude EDC stream into an overhead stream of purified EDC and a bottoms stream of EDC, 1,1,2-trichloroethane, hexachloroethane, hexachlorobenzene, with fouling amounts of chlorinated or oxychlorinated polymeric material. The fouling in the bottoms is severe at EDC levels of below about 30 wt %, and particularly severe at EDC levels of 20 wt % or below. At high EDC levels in the bottoms, EDC acts as a solvent for the fouling materials. The present invention thus permits the EDC unit to operate efficiently at high EDC recovery with corresponding low EDC levels in the bottoms. The Antifoulant functions as a dispersant for the fouling materials in the bottoms thereby inhibiting fouling therein. The present invention enables the EDC unit to operate at relatively long periods of time at EDC levels of 10-25 wt % in the bottoms.

EXPERIMENTS

In order to demonstrate the effectiveness of the antifoulant in the contemplated operations, a thermal fouling test unit (TFT) was used to simulate a crude EDC fouling. In a TFT test, a liquid stream is circulated into a heat exchanger housing a carbon steel heater tube. The heater tube can be heated from 100-1000 degrees F. metal temperature. A high fouling liquid stream will form deposits on the heater surface which results in reducing the liquid outlet temperature which is measured during the test. Decreases in the liquid outlet temperature is a measure of fouling. (i.e. temperature between inlet and outlet increases).

The antifoulant used in the tests was an acylated amine, the reaction product of (a) polyisobutylene having a molecular weight of 900, substituted with succinic anhydride, and (b) a polyamine. This reaction product is referred to a PIBSA-PAM.

The TFT tests were carried out at a temperature of 400 degrees F. The results with PIBSA-PAM in the EDC at a concentration of 200 ppm are presented in TABLE I.

TABLE I

| Antifoulant Type | None | A | A |
|---|---|---|---|
| Antifoulant PPM | None | 200 | 200 |
| Test Time (minutes) | Thermal Fouling ($\Delta T$, F) | | |
| 15 | 15 | 2 | 6 |
| 30 | 18 | 3 | 10 |
| 45 | 19 | 7 | 12 |
| 60 | 24 | 12 | 14 |

Additional tests at a EDC Tar Still of a VCM plant using Antifoulant C (66 wt % overbased magnesium sulfonate and 33 wt % PIBSA-PAM.) The concentration of the Antifoulant C was 200 ppm in the crude EDC and the test temperature was 300 degrees F. The test results are presented in TABLE II. Each test was terminated when energy required to maintain the operating temperature became excessive.

TABLE II

| Antifoulant Type | None | C | C | C | C |
|---|---|---|---|---|---|
| Antifoulant (ppm) | None | 200 | 200 | 200 | 200 |
| Runlength (days) | 3 | 10 | 8 | 12 | 14 |
| Pounds of Crude EDC Stream Processed (1000 pounds) | 300 | 690 | 730 | 900 | 1200 |

The above tests demonstrate the effectiveness of the antifoulant used in accordance with the present invention. The reasons for the improved results are not fully understood but are believed to be due to the effective dispersancy of the incompatible by-product in the crude EDC. The incompatible by-products include highly oxygenated/chlorinated polymeric material (e.g., polyolefin).

What is claimed is:

1. In a method for recovering ethylene dichloride wherein crude ethylene dichloride (EDC) feed stream from a chlorination or oxychlorination unit is distillation separated into an overhead stream of purified ethylene dichloride and a bottoms stream of crude EDC containing fouling amounts of chlorinated and/or oxygenated polymeric materials, the improvement for inhibiting fouling in the bottoms stream comprising introducing into the crude ethylene dichloride feed stream an inhibiting amount of antifoulant selected from the group consisting of (A) the reaction product of (i) an olefin polymer of C2 to C10 mono-olefin having a molecular weight of about 300 to 5000 reacted with a C4 to C10 mono-unsaturated dicarboxylic acid or anhydride material; and (ii) a basic reactant amine;

(B) an oil-soluble magnesium alkyl aromatic sulfonate; and (C) a blend of 10 to 90 wt % (A) and 90 to 10 wt % of (B).

2. The process as defined in claim 1 wherein the acid material is maleic anhydride.

3. The process as defined in claim 2 wherein the olefin polymer is polyisobutylene.

4. The process of claim 1 wherein the basic reactant is a polyamine.

5. The process of claim 4 wherein the polyamine contains from 2 to 60 carbon atoms and 1 to 12 nitrogen groups.

6. The process of claim 4 wherein the polyamine is a polyalkylamine wherein the alkyl groups contain from 2 to 6 carbon atoms and the polyalkylamine contains from 2 to 8 nitrogen atoms per molecule, and wherein 0.2 to 2 moles of said polyamine are reacted per mole of succinic groups.

7. The method of claim 1 wherein the sulfonate is overbased magnesium alkyl benzene sulfonate.

8. The method of claim 7 wherein the alkyl group contains from 12 to 45 carbon atoms.

9. The method of claim 7 wherein the alkyl group contains from 16 to 30 carbon atoms.

10. The method of claim 1 wherein the overbased magnesium sulfonate is overbased with magnesium carbonate to provide an alkalinity of 50 to 700 mg KOH/g.

11. The method of claim 10 wherein the overbased sulfonate has an alkalinity (Total Base Number) of 300 to 600 mg KOH/g.

12. The method of claim 1 wherein the magnesium alkyl aromatic sulfonate has a molecular weight of between 200 and 3000.

13. The method of claim 1 wherein the magnesium sulfonate has the following formula:

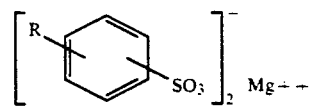

where R is an alkyl having from 12 to 45 carbon atoms.

14. In a method for producing vinyl chloride monomer wherein ethylene dichloride is prepared from chlorination or oxychlorination and then converted to vinyl chloride, the improvement for inhibiting fouling in equipment exposed to crude ethylene dichloride at temperature in the range of 200 to 400 degrees F. comprising, introducing into the crude ethylene dichloride an effective amount of an antifoulant for inhibiting fouling of equipment exposed to crude ethylene dichloride at b temperature between 200 to 400 degrees F., the antifoulant comprising a blend of (a) from 10 to 90 wt % of an acylated polyamine capable of dispersing fouling material in the crude ethylene dichloride, and (b) from 90 to 10 wt % of an overbased magnesium sulfonate having the following formula:

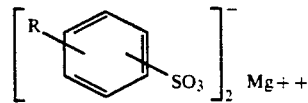

where R is an alkyl having from 12 to 45 carbon atoms.

15. The method of claim 14 wherein the polyamine is polyisobutylene succinic anhydride condensed with polyethylene amine.

* * * * *